United States Patent
Møller et al.

(10) Patent No.: US 9,132,239 B2
(45) Date of Patent: Sep. 15, 2015

(54) DIAL-DOWN MECHANISM FOR WIND-UP PEN

(75) Inventors: Claus Schmidt Møller, Fredensborg (DK); Tom Hede Markussen, Bagsværd (DK); Bo Radmer, Hillerød (DK); Christian Peter Enggaard, Vejby (DK)

(73) Assignee: Novo Nordisk A/S, Bagsvaerd (DK)

( * ) Notice: Subject to any disclaimer, the term of this patent is extended or adjusted under 35 U.S.C. 154(b) by 833 days.

(21) Appl. No.: 13/124,995

(22) PCT Filed: Oct. 21, 2009

(86) PCT No.: PCT/EP2009/063801
§ 371 (c)(1),
(2), (4) Date: Aug. 1, 2011

(87) PCT Pub. No.: WO2010/046394
PCT Pub. Date: Apr. 29, 2010

(65) Prior Publication Data
US 2012/0095410 A1    Apr. 19, 2012

Related U.S. Application Data

(60) Provisional application No. 61/109,242, filed on Oct. 29, 2008.

(30) Foreign Application Priority Data

Oct. 24, 2008   (EP) .................................. 08167547

(51) Int. Cl.
*A61M 5/00*    (2006.01)
*A61M 5/315*   (2006.01)
*A61M 5/20*    (2006.01)

(52) U.S. Cl.
CPC .............. *A61M 5/31525* (2013.01); *A61M 5/20* (2013.01); *A61M 5/3156* (2013.01); *A61M 5/31553* (2013.01)

(58) Field of Classification Search
CPC ....... A61M 5/00; A61M 5/3129; A61M 5/24; A61M 5/2033; A61M 5/3287; A61M 5/32; A61M 5/178; A61M 2005/206
USPC .............................. 604/187, 136, 272, 164.11
See application file for complete search history.

(56) References Cited

U.S. PATENT DOCUMENTS

| | | |
|---|---|---|
| 4,584,439 A | 4/1986 | Paddock |
| 4,924,737 A | 5/1990 | Gummow |

(Continued)

FOREIGN PATENT DOCUMENTS

| | | |
|---|---|---|
| AU | 595723 | 1/1988 |
| CN | 1214292 A | 4/1999 |

(Continued)

OTHER PUBLICATIONS

U.S. Appl. No. 10/610,926 which is owned by the same assignee as U.S. Appl. No. 11/765,789, filed Jun. 20, 2007 by Moller et al.

*Primary Examiner* — Scott Medway
(74) *Attorney, Agent, or Firm* — Wesley Nicolas

(57) ABSTRACT

The present invention relates to a dial-down mechanism for an injection device comprising a torsion spring for assisting injection of a dose of medicament from the injection device, the dial-down mechanism comprising a ratchet arm (21) engaging a ring element (10) and a reset element (30) which acts on a knob located on the periphery of the ratchet arm (21) to move the ratchet arm (21) out of engagement with the ring element (10) in order to allow the set dose to be reduced.

3 Claims, 3 Drawing Sheets

(56) References Cited

U.S. PATENT DOCUMENTS

| | | | |
|---|---|---|---|
| 4,998,922 A * | 3/1991 | Kuracina et al. | 604/192 |
| 5,011,479 A * | 4/1991 | Le et al. | 604/198 |
| 5,104,380 A | 4/1992 | Holman et al. | |
| 5,154,698 A * | 10/1992 | Compagnucci et al. | 604/110 |
| 5,480,387 A | 1/1996 | Gabriel et al. | |
| 5,514,097 A | 5/1996 | Knauer | |
| 6,004,297 A | 12/1999 | Steenfeldt-Jensen et al. | |
| 6,221,046 B1 | 4/2001 | Burroughs et al. | |
| 7,686,786 B2 | 3/2010 | Moller et al. | |
| 7,771,399 B2 | 8/2010 | Burren et al. | |
| 8,048,037 B2 | 11/2011 | Kohlbrenner et al. | |
| 8,202,256 B2 | 6/2012 | Moller | |
| 8,206,361 B2 | 6/2012 | Moller | |
| 8,267,899 B2 | 9/2012 | Moller | |
| 2002/0002354 A1* | 1/2002 | Vetter et al. | 604/272 |
| 2002/0173752 A1 | 11/2002 | Polzin | |
| 2003/0040715 A1 | 2/2003 | D'Antonio et al. | |
| 2003/0050609 A1 | 3/2003 | Sams | |
| 2004/0199117 A1 | 10/2004 | Giambattista et al. | |
| 2005/0090782 A1 | 4/2005 | Marshall et al. | |
| 2007/0167916 A1* | 7/2007 | Lee et al. | 604/187 |
| 2007/0265568 A1* | 11/2007 | Tsals et al. | 604/136 |
| 2008/0306445 A1 | 12/2008 | Burren et al. | |
| 2008/0312592 A1* | 12/2008 | Barrow-Williams et al. | 604/136 |
| 2013/0204197 A1* | 8/2013 | Bicknell et al. | 604/197 |

FOREIGN PATENT DOCUMENTS

| | | |
|---|---|---|
| DE | 29513214 U1 | 1/1997 |
| DE | 19838760 A1 | 4/2000 |
| DE | 10103287 A1 | 8/2001 |
| DE | 20209051 U1 | 4/2003 |
| DE | 10237258 A1 | 3/2004 |
| EA | 008160 | 4/2007 |
| EP | 327910 A2 | 8/1989 |
| EP | 0608343 A1 | 8/1994 |
| EP | 615762 | 9/1994 |
| EP | 897729 A2 | 2/1999 |
| EP | 908273 | 4/1999 |
| EP | 937476 | 8/1999 |
| EP | 1768725 A1 | 4/2007 |
| EP | 1909871 A1 | 4/2008 |
| EP | 1926514 A1 | 6/2008 |
| EP | 2373361 A1 | 10/2011 |
| GB | 574705 | 1/1946 |
| JP | 2008-528071 A | 7/2008 |
| JP | 2008-196696 A | 8/2008 |
| PL | 1804865 | 10/2005 |
| PL | 2373361 | 9/2012 |
| RU | 2254878 C2 | 6/2005 |
| SU | 1528330 A3 | 12/1989 |
| WO | 95/21645 A1 | 8/1995 |
| WO | 02/50214 A2 | 6/2002 |
| WO | WO02053214 | 7/2002 |
| WO | 03/057285 A2 | 7/2003 |
| WO | 2004054644 A1 | 7/2004 |
| WO | 2005/102421 A1 | 11/2005 |
| WO | 2006/003130 A1 | 1/2006 |
| WO | 2006040296 A2 | 4/2006 |
| WO | 2006045526 A1 | 5/2006 |
| WO | WO2006045526 | 5/2006 |
| WO | 2007021195 A1 | 2/2007 |
| WO | 2007063342 A1 | 6/2007 |
| WO | 2007104636 A1 | 9/2007 |

\* cited by examiner

DIAL-DOWN MECHANISM FOR WIND-UP PEN

CROSS-REFERENCE TO RELATED APPLICATIONS

This application is a 35 U.S.C. §371 national stage application of International Patent Application PCT/EP2009/063801 (published as WO 2010/046394), filed Oct. 21, 2009, which claimed priority of European Patent Application EP 08167547.2, filed Oct. 24, 2008; this application further claims priority under 35 U.S.C. §119 of U.S. Provisional Application 61/109,242, filed Oct. 29, 2008.

THE TECHNICAL FIELD OF THE INVENTION

The present invention relates to a dial-down mechanism for automatic wind-up pens. In particular, the present invention relates to an integrated dial-down mechanism for a torsion spring assisted wind-up pen.

DESCRIPTION OF RELATED ART

In known injection devices, such as wind-up pens, based on torsion springs, the user usually strains the torsion spring by rotating a rotatable dose setting member of the injection device. The force thereby applied by the user is stored in the torsion spring for later release.

An example of a known wind-up pen applying a torsion spring may for example be found in U.S. Pat. No. 5,104,380. In this wind-up pen the dose setting member is located at the proximal end and works such that when the user rotates the dose setting member the spring is strained. The wind-up pen disclosed in U.S. Pat. No. 5,104,380 has the disadvantage that if a user sets a dose to large it is not possible to decrease the set dose. The user then has to release the latch mechanism thereby expelling the entire set dose before a new correct dose can be set and delivered.

Modern injection devices as the one e.g. disclosed in U.S. Pat. No. 6,004,297 has the possibility of rotating the dose setting member in an opposite direction and thereby reduce the set dose prior to deliverance of the set dose. Such mechanism is usually referred to as a dial-up/dial-down mechanism since it can both increase and decrease the set dose prior to injection.

Such dial-up/dial-down mechanism for a spring-loaded injection pen is known from WO 02/053214.

A wind-up pen based on a torsion spring and with a dial-up/dial-down mechanism is further disclosed in WO 2006/045526. The mechanism described in this document is based on a number of cam and key engagements. When working within small dimensions as in injection devices it has shown that such small dimensioned cam and key parts has a tendency to break during manufacture or during use.

DESCRIPTION OF THE INVENTION

It is an object of the present invention to provide a dial-down mechanism for automatic wind-up pens which is more robust and less vulnerable to breakage.

The ratchet arm provided on the dose setting tube engages one or more teeth on the fixation element. Further the ratchet arm is provided with a radially extending knob or the like which when moved radial inwardly moves the ratchet arm out of its engagement with the fixation element. The knob on the ratchet arm is moved inwardly by a reset element provided on a reset tube. Once the reset element sweeps over the knob it moves the ratchet arm inwardly. By having the reset element of the reset member work directly on the periphery of the knob and having the knob extend into the orbit described by the reset element small parts engaging each other can be avoided. The reset element can have many different shapes as long as it has the ability to move the ratchet arm out of engagement with the fixation element. Preferably the reset element is a prolongation on the reset tube extending distally from the reset tube such that the predominant part of the reset tube can be housed inside the dose setting tube but with the reset element extending out of the dose setting tube. The engagement between the knob of the ratchet arm and the reset element is designed such that a relative rotation between these two parts results in a inwardly radial movement of the ratchet arm which then is moved out of engagement with the teeth of the fixation element. The fixation element is preferably coupled to the housing of the injection device in a non-rotatable manner through engaging fins located on the external surface of the fixation element. These fins are rotational locked in similar grooves provided on the inside surface of the housing or an element functionally working as a part of the housing, however the fixation element can be moved axially out of its engagement with the housing and into an engagement with a drive element such that the torsional force accumulated in the torsion spring can be delivered to this drive element in order to drive a liquid out of the injection device.

Preferably, the reset element is rotated around the centre axis of the injection pen with a constant radius while the ratchet arm has its knob extending beyond this diameter such that the reset element can be brought into engagement with the knob whereby the ratchet arm is moved out of engagement with the fixation element.

Further the ratchet arm is provided with a steep surface on its free end which engages a steep surface of a tooth of the fixation element. When these two steep surfaces are brought out of engagement, the two elements can rotate relatively to each other.

DEFINITIONS

An "injection pen" is typically an injection apparatus or device having an oblong or elongated shape somewhat like a pen for writing. Although such pens usually have a tubular cross-section, they could easily have a different cross-section such as triangular, rectangular or square or any variation around these geometries.

As used herein, the term "medicament" or "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the dial down mechanism including the ring shaped element 10 whereas the term "proximal end" is meant to refer to the opposite end pointing away from the ring shaped element 10.

Figure 1:
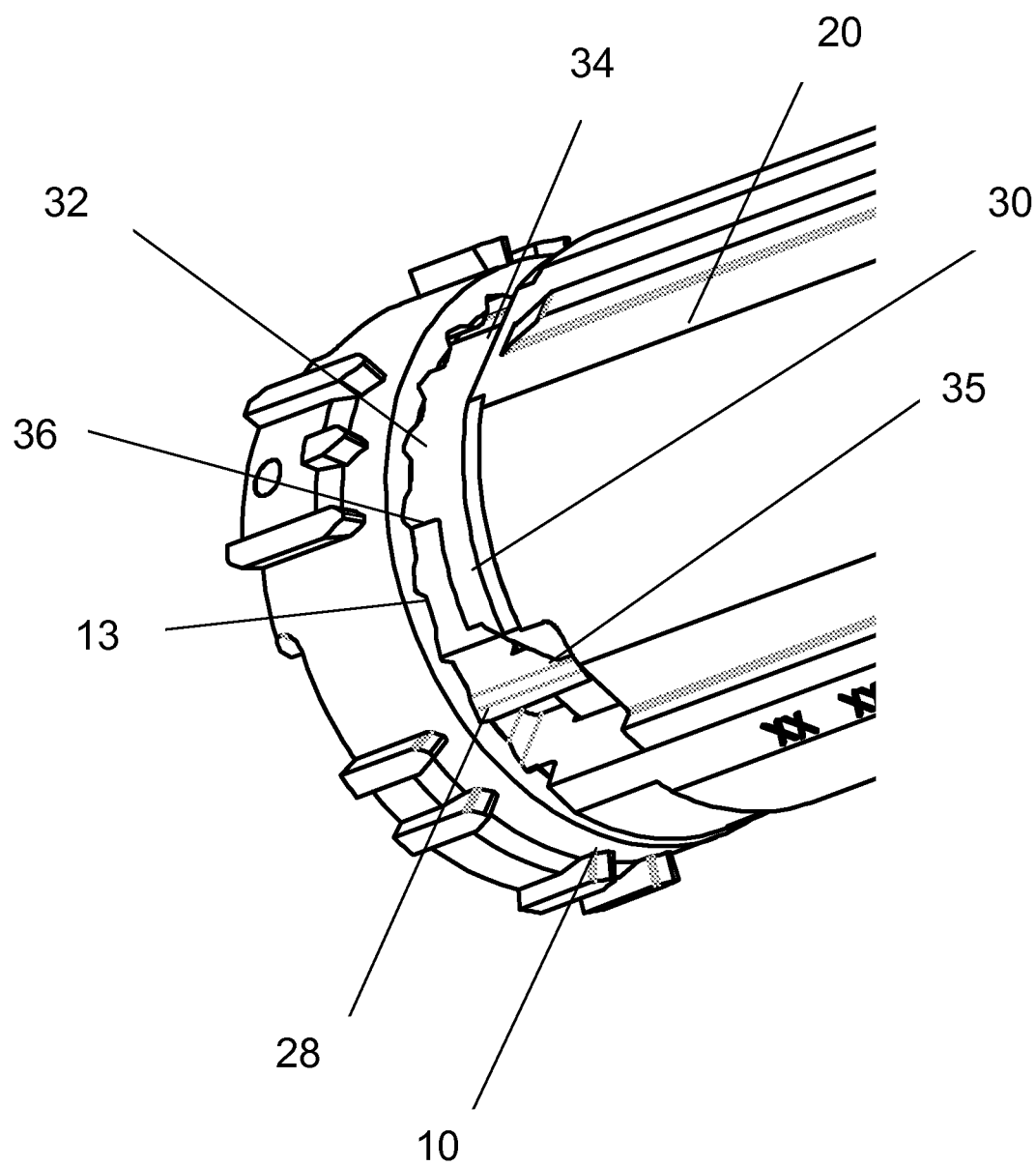
FIG. 1 Show an example of the dial-down mechanism.

The dial down mechanism disclosed in FIG. 1 comprises of three parts, a fixation element or ring 10, a dose setting element or ratchet tube 20 and a reset tube 30.

Figure 3:
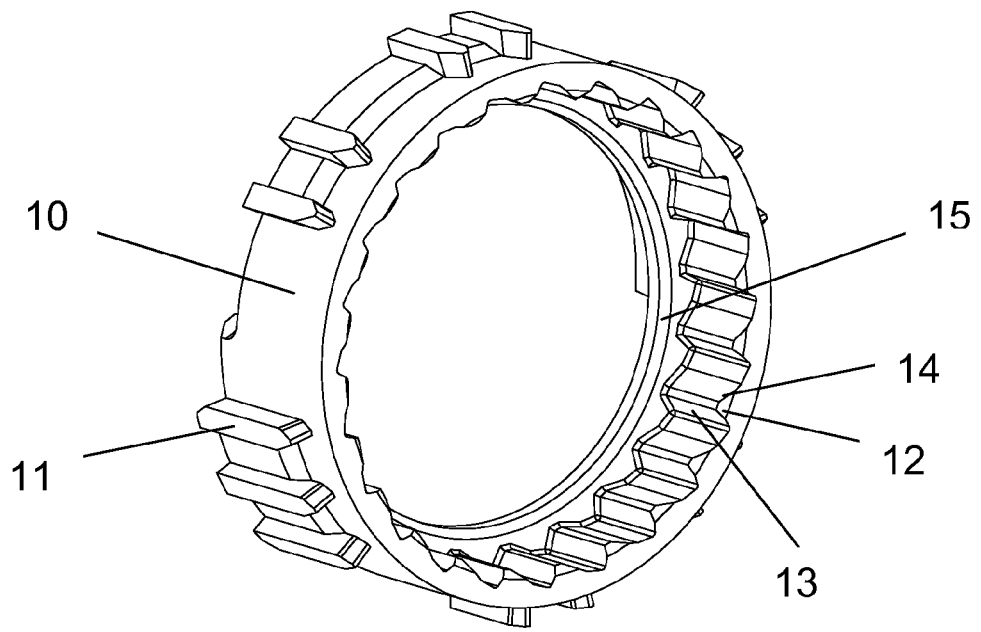
FIG. 3 Show a view of the fixation element in a ring-shaped configuration.

The ring 10 as disclosed in FIG. 3 has on its outside surface a number of engaging means such as fins 11 by which the ring 10 is non-rotatable coupled to a not shown housing of an injection device. The ring 10 could alternatively be attached to the housing in a number of different ways, however, as explained later the ring shaped element 10 must be able to move axially relatively to the housing.

Figure 2:
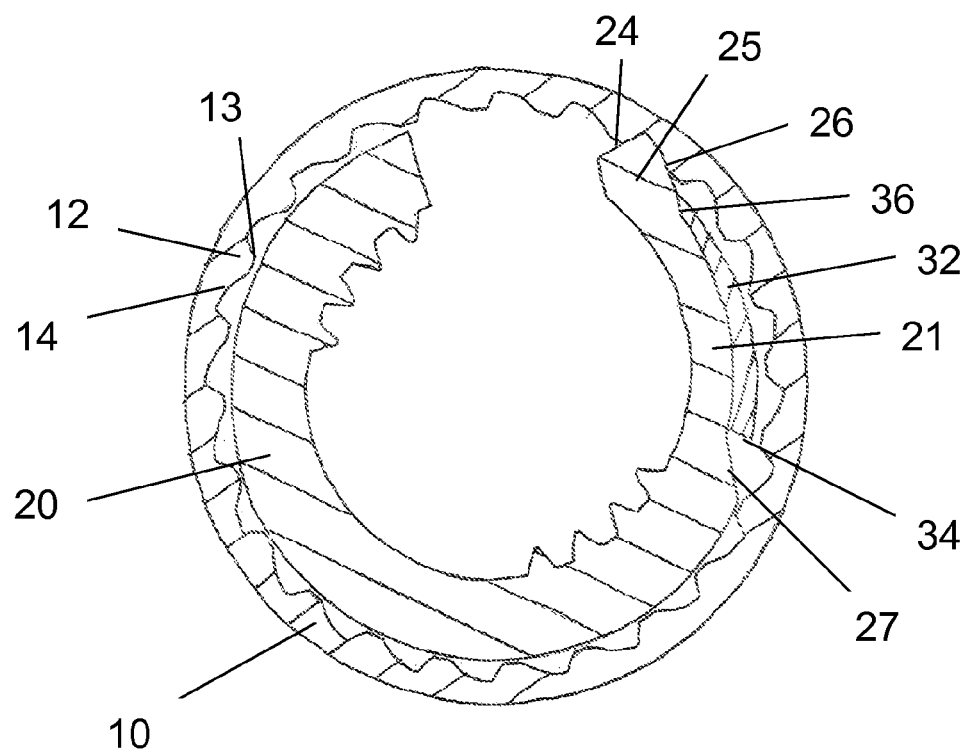
FIG. 2 Show a sectional view of the dial-down mechanism.

On its inside surface the ring 10 is provided with a plurality of teeth 12 which has a steep edge 13 in one direction and a sloped edge 14 in the opposite direction such that the ratchet arm 21 of the ratchet tube 20 is prevented from rotating in one direction but is allowed to rotate in the opposite direction. This is best seen in FIG. 2.

Figure 4:
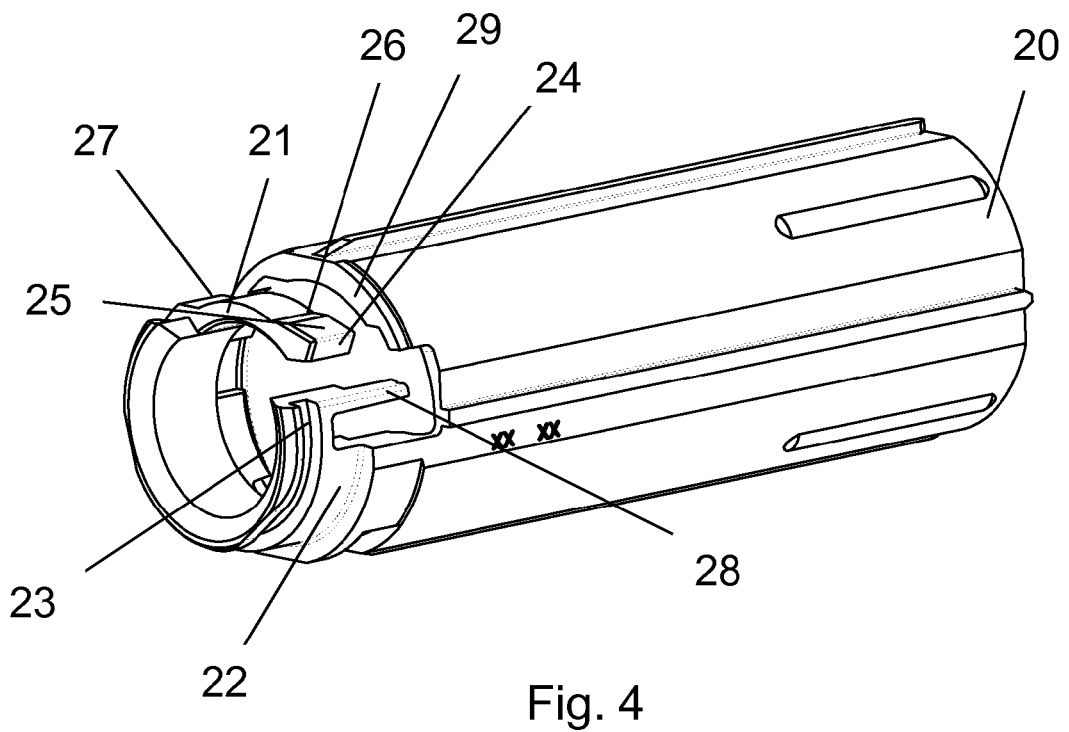
FIG. 4 Show a view of the ratchet tube.

The ratchet tube 20 disclosed in details on FIG. 4 has on its distal end a circular part with a peripheral outer surface 22 that fits into the inside of the ring 10. This outer surface 22 is provided with a circular recess 23 which is engaged with a similar circular element 15 on the ring 10 such that the ring 10 and the ratchet tube 20 is locked to each other in the axial direction but can be rotated relatively to each other.

The peripheral outer surface 22 is provided with a flexible ratchet arm 21 which terminates in a steep surface 24. The ratchet arm 21 is on its peripheral surface provided with an outwardly pointing protrusion 25 which opposite the steep surface 24 which steep surface 24 also incorporates the protrusion 25 has a sloped surface 26 which slopes down to the ratchet arm 21.

Once the ratchet tube 20 and the ring 10 is engaged as disclosed in FIG. 1 the steep surface 24 of the ratchet arm 21 engages the steep edge 13 on the ring 10 such that the ratchet tube 20 can only be rotated relatively to the ring 10 in one direction which in FIG. 1 is in the clockwise direction.

The ratchet tube 20 is engaged with a not shown torsion spring which at its opposite end is connected to the housing of the injection device such that when the ratchet tube 20 is rotated in the clockwise direction (seen from a proximal position) the torsion spring is strained and is held in this strained position by the engagement between the steep surface 24 of the ratchet arm 21 and the steep edge 13 of the teeth 12 on the ring 10.

In this way a user can strain the torsion spring and thereby set a dose by rotating the ratchet tube 20 relatively to the ring 10 in the clockwise direction and the described engagement 24, 13 makes it impossible for the torsion spring to rotate back the ratchet tube 20.

Figure 5:
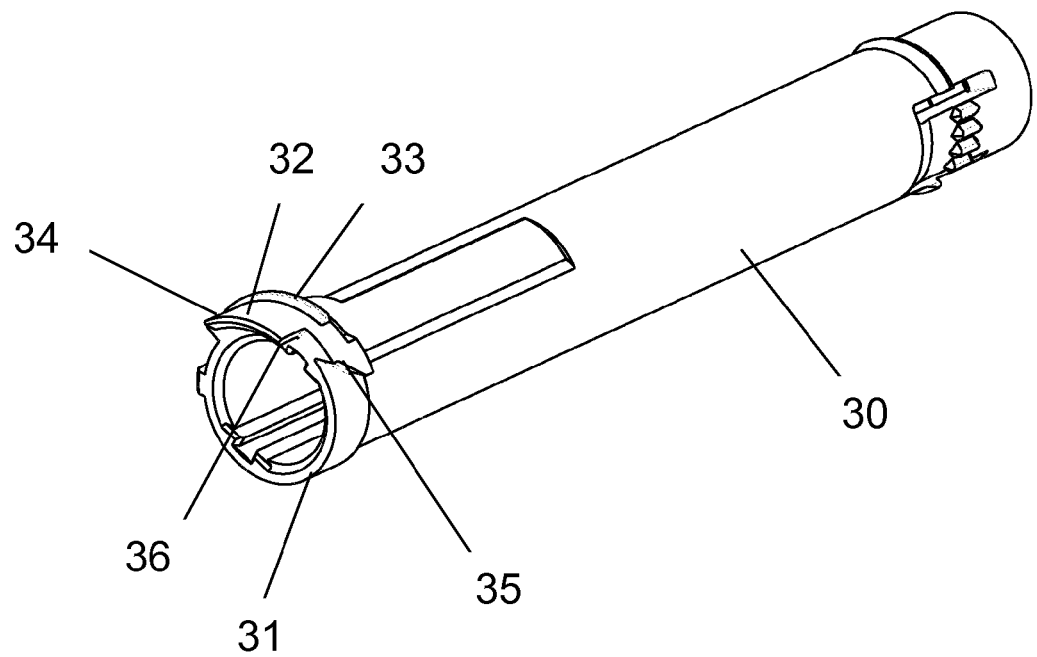
FIG. 5 Show a view of the reset tube.

In order to provide a possibility for the user to dial down the set dose, a reset tube 30 is provided. In relation to FIG. 5 the reset tube 30 is provided with an extended portion 31 which has a forwardly pointing reset element 32 which follows the periphery of the extended portion 31.

Once the injection device is assembled the reset tube 30 is fitted inside the ratchet tube 20 such that the reset element 32 is located above the ratchet arm 21 as depictured in FIGS. 1 and 2. In this position the axial engagement between the ratchet tube 20 and the reset tube 30 is secured by the protrusion 33 of the reset tube 30 engaging in front of the front surface 29 of the ratchet tube 20.

The extended portion 31 of the reset tube 30 is further provided with a first surface 34 in the clockwise direction and a second surface 35 in the anti-clockwise direction. Further, the reset element 32 is provided with a reset surface 36 in the anti-clockwise direction.

The first surface 34 engages a similar dial-up surface 27 on the ratchet tube 20 such that rotation of the reset tube 30 is clockwise direction is transformed directly to the ratchet tube 20 meaning that when a user dials the reset tube 30 in the clockwise direction to set a dose the ratchet tube 20 follows this rotation and rotates relatively to the ring 10.

The second surface 35 engages a spring element 28 urging the reset tube 30 in the clockwise direction whereas the reset surface 36 of the reset element 32 engages the sloped surface 26 of the protrusion 25 of the ratchet arm 21.

When setting a dose as explained above the user rotates the reset tube 30 which rotation is passed on to the ratchet tube 20 which again is allowed to rotate relatively to the ring 10 in the clockwise direction thereby straining the torsion spring.

When a user regrets the set dose and wants to decrease the set dose this is done by rotating the reset tube 30 in the anti-clockwise direction. By doing so—as depictured in FIG. 2—the reset surface 36 is pressed against the sloped surface 26 of the protrusion 25 which pulls the steep surface 24 out of engagement with the steep edge 13 of the teeth 12. This allows the torsion spring to be released and force the ratchet tube 20 in the anti-clockwise direction. Due to the size of the torque stored in the torsion spring, the ratchet tube 20 will be moved faster than the reset tube 30 whereby the sloped surface 26 of the protrusion 25 will no longer have the pressure of reset surface 36 resting on it and the flexible ratchet arm 21 will flex to its initial position and the steep surface 24 will engage the next steep edge 13 of the next teeth 12. By a continued anti-clockwise rotation of the reset tube 30, the steep surface 24 will move from teeth 12 to teeth 12 in a continued movement thereby lowering the torque stored in the torsion spring.

Once the correct setting is obtained the torque stored in the torsion spring is released by axially moving the ring 10 out of engagement with the housing, whereby the torsion spring rotates back all three elements 10, 20, 30.

Some preferred embodiments have been shown in the foregoing, but it should be stressed that the invention is not limited to these, but may be embodied in other ways within the subject matter defined in the following claims, e.g. could a needle assembly as herein described be delivered to the user in a rigid and sterile container which further could be shaped as a tool for assisting the user in mounting the needle assembly on to the injection device.

The invention claimed is:

1. A dial-down mechanism for an injection device comprising a torsion spring which is strained when setting a dose by rotating a dose setting member (20) relatively to a housing in a first direction, and unstrained when rotating the dose setting member (20) in a second direction opposite the first direction, the torsion spring for storing energy to expel a dose from the injection device, the dial-down mechanism comprising:
    a fixation element (10) coupled to the housing and having a plurality of inwardly pointing teeth (12),
    at least one ratchet arm (21) coupled to the dose setting member (20),
    wherein the at least one ratchet arm (21) engages the teeth (12) of the fixation element (10) and is shaped such that the dose setting member (20) is prevented from rotating in the second direction when the ratchet arm (21) engages the teeth (12) of the fixation element (10),
    the dial-down mechanism further comprises a reset member (30) configured for movement in a first direction and a second direction opposite the first direction, such that rotation of the reset member (30) in the first direction to set a dose is transformed directly to the dose setting member (20) and thereby rotates relatively to the fixation element (10), and rotation of the reset member (30) in the second direction activates the ratchet arm (21) to disengage the fixation element (10) and thereby allow the dose setting member (20) to rotate in the second direction by carrying at least one forward extending reset element (32) located distally to the reset member (30) and which acts on at least one part (25) of the ratchet arm to move the ratchet arm (21) out of engagement with the teeth (12) of the fixation element (10) thereby dialing down the set dose, wherein
    the reset member (30) is at least partially provided inside the dose setting tube (20) and axially retained by the dose setting member (20), and
    the ratchet arm (21) carries at least part (25) extending radially from the at least one ratchet arm (21) and having an outer radius from the centre axis of the injection device larger than the outer radius of the remaining part of the ratchet arm (21).

2. A dial-down mechanism according to claim 1, characterized in that, the reset element (32) travels along a constant radius from the centre axis of the injection device when rotated.

3. A dial-down mechanism according to claim 1, characterized in that, the ratchet arm (21) is provided with a steep surface (24) engaging a steep surface (13) of the teeth (12) of the fixation element (10).

* * * * *